United States Patent [19]
Hedengren et al.

[11] Patent Number: 5,717,332
[45] Date of Patent: Feb. 10, 1998

[54] SYSTEM AND METHOD USING EDDY CURRENTS TO ACQUIRE POSITIONAL DATA RELATING TO FIBERS IN A COMPOSITE

[75] Inventors: **Kristina Helena Valborg Hedengren;
Richard Oscar McCary**, both of Schenectady, N.Y.

[73] Assignee: General Electric Company, Schenectady, N.Y.

[21] Appl. No.: 787,650

[22] Filed: Jan. 23, 1997

Related U.S. Application Data

[63] Continuation of Ser. No. 55,597, May 3, 1993, abandoned.

[51] Int. Cl.$^6$ .............................. G01B 7/26; G01N 27/72
[52] U.S. Cl. .............................. 324/229; 364/563
[58] Field of Search ................. 324/229, 242, 324/207.11, 207.16, 207.17, 207.15, 243, 230, 231, 232, 225, 234, 228, 239; 364/563, 556, 560, 570

[56] References Cited

U.S. PATENT DOCUMENTS

| | | | |
|---|---|---|---|
| 4,004,693 | 1/1977 | Tsuji et al. | 324/207.22 |
| 4,255,709 | 3/1981 | Zatsepin et al. | 324/229 |
| 4,438,754 | 3/1984 | Nanny et al. | 324/207.26 |
| 4,763,071 | 8/1988 | McGee et al. | 324/233 |
| 4,783,695 | 11/1988 | Eichelberger et al. | 357/65 |
| 4,894,617 | 1/1990 | Urbani | 324/243 |
| 4,904,939 | 2/1990 | Mian | 324/229 |
| 5,062,298 | 11/1991 | Falcoff et al. | 324/231 |
| 5,182,513 | 1/1993 | Young et al. | 324/232 |
| 5,237,271 | 8/1993 | Hedengren | 324/232 |
| 5,278,498 | 1/1994 | Vernon et al. | 324/234 |
| 5,315,234 | 5/1994 | Sutton, Jr. et al. | 324/242 |
| 5,371,461 | 12/1994 | Hedengren | 324/242 |

FOREIGN PATENT DOCUMENTS

| | | | |
|---|---|---|---|
| 2257528 | 1/1993 | United Kingdom | 324/229 |

OTHER PUBLICATIONS

U.S. Patent application S.N. 07/696,457, entitled "An Apparatus and Method for Non–destructive Testing Using Multi–frequency Eddy Currents" by Kristina H. Hedengren, filed May 6, 1991.

U.S. Patent Application S.N. 07/865,786, entitled "Flexible High Density Interconnect Structure and Flexibly Interconnected System" by C.W. Eichelberger et al., filed Apr. 7, 1992.

U.S. Patent Application S.N. 07/696,455, entitled "Flexible Eddy Current Surface Measurement Array for Detecting Near Surface Flaws in a Conductive Part" by K.H. Hedengren et al., filed May 6, 1991.

Primary Examiner—Sandra L. O'Shea
Assistant Examiner—Roger C. Phillips
Attorney, Agent, or Firm—David C. Goldman; Marvin Snyder

[57] ABSTRACT

A system and method for determining fiber-depth of at least one layer of reinforcing fibers within an electrically conductive workpiece is provided. The system comprises an eddy current probe having one or more eddy current elements for generating a respective electrical signal indicative of a spacing with respect to a predetermined section of the reinforcing fibers. A signal processor is connected to the eddy current probe to receive and to process each spacing-indication electrical signal so as to generate data indicative of fiber-depth of the predetermined section relative to a workpiece surface. A display device may be connected to the signal processor to provide visual indicia representative of the fiber depth. Further a controller may be connected to receive and store the fiber-depth data which can be used by a machining device for selectively removing material from the workpiece surface, in accordance with the stored fiber-depth data. The eddy current elements may form a substantially colinear row of eddy current elements each cooperating to determine the actual fiber axis orientation of reinforcing fibers within the workpiece.

7 Claims, 3 Drawing Sheets

SYSTEM AND METHOD USING EDDY CURRENTS TO ACQUIRE POSITIONAL DATA RELATING TO FIBERS IN A COMPOSITE

This application is a Continuation of application Ser. No. 08/055,597 filed May 3, 1993 now abandoned.

BACKGROUND OF THE INVENTION

The present invention relates to a system and method for nondestructive inspection of a workpiece and, more particularly, to eddy current inspection of an electrically conductive workpiece, such as a metal matrix composite (MMC), for measuring and selectively controlling fiber-depth of at least one layer of reinforcing fibers embedded within the workpiece.

Typically, MMC refers to a material which comprises a metal, such as titanium or other suitable metal alloy, that is structurally strengthened by a reinforcing constituent, for example, reinforcing fibers of graphite, silicon carbide, boron, or other suitable materials. Briefly, a commonly used MMC fabrication technique may involve repetitively winding one or more layers of reinforcing fibers on a drum and then plasma-spraying the metal onto the drum-wound fiber layer to form a laminate MMC workpiece. To improve the structural strength of the MMC workpiece as well as to achieve weight reduction, it is desirable to increase the fiber-to-metal volume ratio in the workpiece.

To increase the fiber-to-metal volume ratio it would be advantageous to provide a system and method capable of accurately and precisely measuring in a nondestructive manner the fiber-depth of a predetermined layer of reinforcing fibers relative to a surface of the plasma-sprayed workpiece. For instance, fiber-depth data could then be effectively used to control an appropriate machining device to selectively remove excess metal from the workpiece surface so as to provide a selected spacing between the workpiece surface and the predetermined layer of reinforcing fibers. The selected spacing in effect could be precisely controlled to optimize fiber-to-metal volume ratio. Further, since optimum structural properties are generally achieved when the reinforcing fibers in the workpiece are oriented substantially along one predetermined fiber-axis direction, it is also desirable to provide a system and method capable of determining the actual fiber-axis orientation of reinforcing fibers in the workpiece.

Although eddy current inspection techniques have been proposed to nondestructively inspect MMCs, significant disadvantages remain. Eddy current inspection techniques proposed heretofore, in general, have been limited either to merely monitor the overall fiber-to-metal volume ratio of the workpiece under inspection or to measure the overall thickness of the workpiece or to count the number of fiber layers therein. However, such eddy current inspection techniques have not been used to determine the actual geometric positioning of the embedded reinforcing fibers (i.e., fiber-depth and fiber-axis orientation). These are important disadvantages being that fiber-depth data and fiber-axis orientation can be advantageously utilized, as previously described, to effectively increase the fiber-to-metal volume ratio of the workpiece and to characterize the structural integrity thereof.

Accordingly, it is an object of the present invention to provide a system and method for nondestructively measuring fiber-depth in an electrically conductive workpiece having at least one layer of reinforcing fibers.

It is a further object of the present invention to provide a system and method which uses fiber-depth data for providing a selected spacing between the workpiece surface and a predetermined layer of reinforcing fibers.

It is yet a further object of the present invention to provide a system and method for determining actual fiber-axis orientation of reinforcing fibers in the workpiece.

SUMMARY OF THE INVENTION

The foregoing and further objects of the present invention will become apparent as the description proceeds. In accordance with the present invention, a system and method for nondestructively determining fiber-depth of at least one layer of reinforcing fibers within an electrically conductive workpiece, such as a MMC, is provided. The system comprises eddy current probe means for generating a respective electrical signal indicative of a spacing with respect to a predetermined section of the reinforcing fibers when the probe means is positioned adjacent to a surface of the workpiece. A signal processor is connected to the eddy current probe means to receive and to process the respective spacing-indication electrical signal, so as to generate data indicative of fiber-depth of the predetermined section relative to the workpiece surface, in accordance with the processed electrical signal.

In one embodiment of the invention, a display device may be connected to the signal processor to provide visual indicia representative of the fiber-depth. In another embodiment of the invention the system may further comprise a controller connected to the signal processor to receive and store the fiber-depth data. Machining means can be operatively coupled to the controller for selectively removing metal material from the workpiece surface to provide a selected spacing between the predetermined section of reinforcing fibers and the machined workpiece surface, in accordance with the stored fiber-depth data. In yet another embodiment of the invention, the eddy current probe means may comprise a spatially correlated array of eddy current elements including, for example, at least one substantially colinear row of eddy current elements adapted to reach a predetermined inspection position being substantially parallel to a predetermined fiber-axis, each eddy current element in that substantially colinear row cooperates to generate respective spacing-indication electrical signals indicative of the actual fiber-axis orientation of predetermined ones of the reinforcing fibers in the workpiece. The array of eddy current elements can be flexibly made, preferably using a photolithographic process, and can be accommodated in a flexible housing which in cooperation with biasing means allows the array to conform to a workpiece having a substantially curved surface. Each eddy current element therein may comprise one or more sense coils preferably interconnected in an absolute mode. Predetermined ones of the sense coils can be adapted to generate respective spacing-indication electrical signals in response to a selected operating frequency 'tuned' according to the specific constituent components of the workpiece undergoing inspection.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following detailed description in conjunction with the accompanying drawings in which like numerals represent like parts throughout the drawings, and in which:

DETAILED DESCRIPTION OF THE INVENTION

Figure 1:
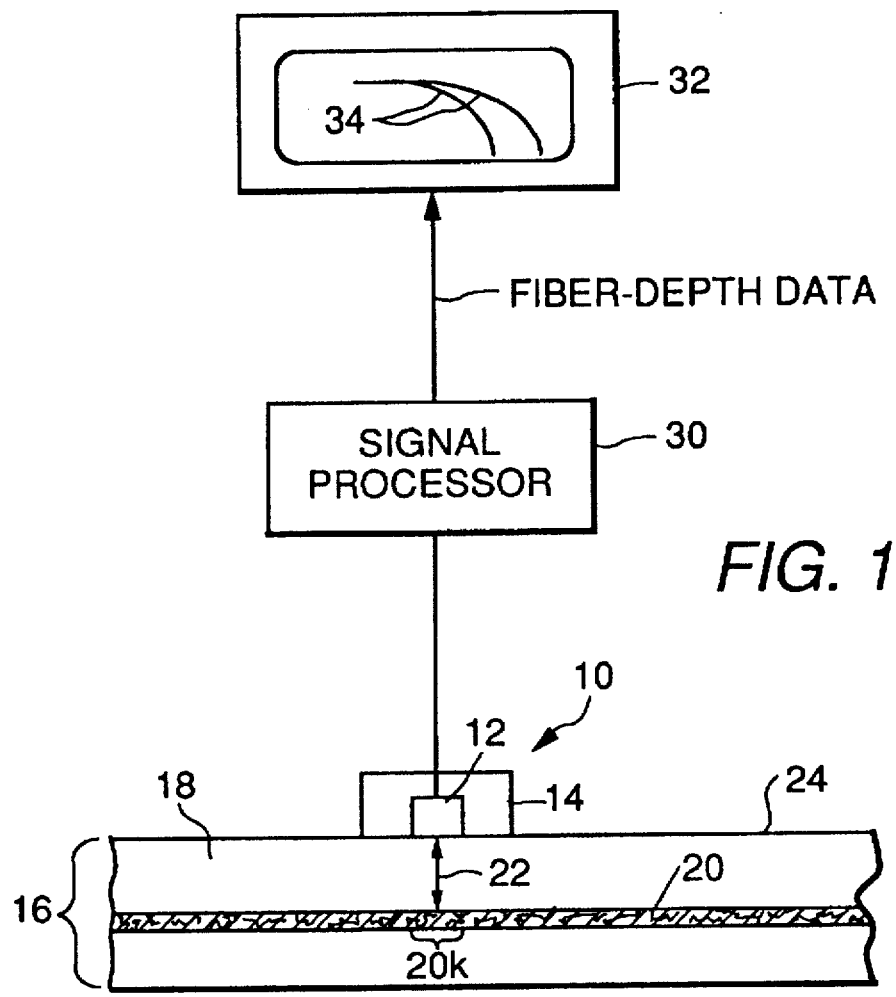
FIG. 1 is a schematic representation of an eddy current inspection system according to one embodiment of the present invention.

A nondestructive inspection system according to the present invention, as illustrated in FIG. 1, comprises an eddy current probe 10 which includes at least one eddy current element 12 enclosed within a housing 14. Eddy current element 12 cooperates with at least one associated drive coil (not shown) electrically corrected to an appropriate electrical source for establishing an inducing time-varying magnetic field in a manner well understood by those skilled in the art. The inducing magnetic field establishes an eddy current flow in an electrically conductive workpiece 16 under inspection and the eddy current flow in turn establishes a reflected magnetic field which is inductively coupled to eddy current element 12. Workpiece 16 is shown, by way of example and not by way of limitation, as a metal matrix composite (MMC) which comprises a metal 18, such as titanium or other suitable metal, being structurally strengthened by at least one layer of reinforcing fibers 20 having a respective electrical conductivity different than the electrical conductivity of the metal. Accordingly, the presence of the layer of reinforcing fibers 20 in workpiece 16 causes a certain change to the electrical conductivity encountered by the eddy current flow which in turn changes the reflected magnetic field coupled to the eddy current element. For a given spatial positioning of the eddy current probe 10 relative to the layer of reinforcing fibers 20, and for a given operating frequency of the electrical source coupled to the drive coil therein, the change to the reflected magnetic field causes eddy current element 12 to generate a respective electrical signal indicative of a spacing 22 between fiber 20 and workpiece surface 24 with respect to at least a predetermined section $20_k$ of the reinforcing fibers 20. For example, this is accomplished by placing eddy current probe 10 in contact with surface 24 of workpiece 16.

Figure 2:
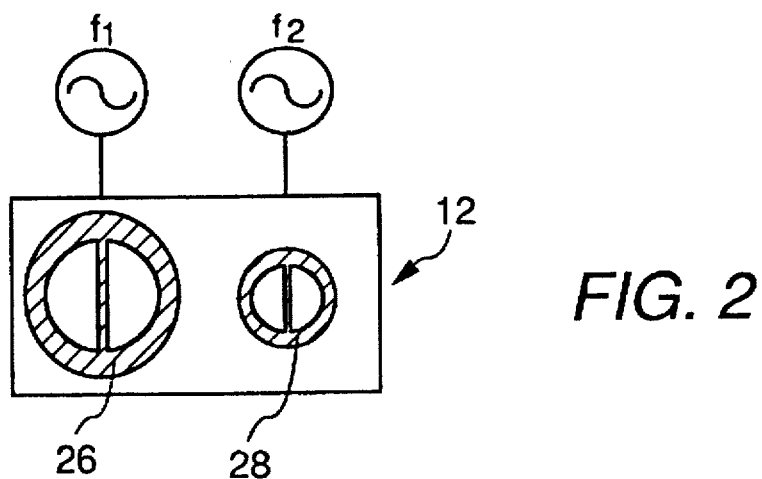
FIG. 2 shows a schematic top plan view of exemplary eddy current elements used in the present invention.

FIG. 2 shows details about a typical eddy current element 12 which can be used in the exemplary embodiment of the eddy current probe shown in FIG. 1. As illustrated in FIG. 2, each eddy current element 12 includes one or more sense coils 26 and 28 constituting a respective metallized pattern electrically responsive to the reflected magnetic field so as to produce a respective spacing-indication electrical signal. Preferably each eddy current element operates in an absolute mode, that is, each eddy current element has its respective sense coil connected to produce an electrical signal suitable to indicate spacing variations between the workpiece surface and the layer of reinforcing fibers 20.

As is well understood by those skilled in the art, the density of the eddy current flow in the workpiece varies as a function of distance from the surface directly beneath the eddy current probe. For example, the distance at which the density of the eddy current flow is reduced to a level of about 37% of the surface density is generally defined as the standard depth of penetration. For a given material, the depth of penetration is inversely proportional to the square root of the operating frequency of the inducing magnetic field. Thus, the eddy current probe may be selected to operate at predetermined frequencies chosen according to the particular composition of the workpiece under inspection. The reader is referred to allowed U.S. patent application Ser. No. 07/696,457, entitled "An Apparatus and Method for Non-destructive Testing Using Multi-frequency Eddy Currents" by Kristina H. Hedengren; this allowed application being assigned to the same assignee of the present invention is incorporated herein by reference. Briefly, the above incorporated application provides a detailed discussion of operationally tailoring the range of depth of penetration through multi-frequency operation of the eddy current probe. This multi-frequency operation can be used to 'tune' fiber-depth detection depending on the electrical conductivity of the workpiece under inspection. Accordingly, sense coils 26 and 28 may be respectively designed to individually cooperate with an associated drive coil in response to a particular predetermined operating frequency. For instance sense coil 26 may be responsive to a predetermined operating frequency $f_1$ while sense coil 28 may be responsive to a different predetermined operating frequency $f_2$. It will be appreciated by those skilled in the art that sense coils 26 and 28 may also be operated as drive coils by means of appropriate drive electronics.

FIG. 1 further shows a signal processor 30 connected to the eddy current element 12 by suitable electrical leads to receive the respective spacing-indication electrical signal. For simplicity of illustration, FIG. 1 illustrates only one eddy current element; it should be appreciated, however, that probe 10 can include an array of spatially correlated eddy current elements. Accordingly, the signal processor may be similar to the multichannel eddy current data acquisition system described in U.S. Pat. No. 5,182,513 entitled "Method and Apparatus for a Multichannel Multifrequency Data Acquisition System for Nondestructive Eddy Current Inspection Testing" by J. D. Young et al., assigned to the assignee of the present invention and hereby incorporated by reference. Briefly, the signal processor processes a received spacing-indication electrical signal to generate data indicative of fiber-depth of at least the predetermined section $20_k$ of reinforcing fibers 20 with respect to workpiece surface 24. In the case of a spatially correlated array of eddy current elements, signal processor 30 provides a multiplexing capability for simultaneously processing each spacing-indication electrical signal received from the eddy current probe 10. It will be further appreciated that a spatially correlated army improves fiber-depth detection sensitivity, as well as inspection productivity. For example, additional predetermined sections of a respective layer of reinforcing fibers can be simultaneously inspected by such an array of eddy current elements in cooperation with the multichannel signal processor described in full detail in the foregoing incorporated patent. Further, an array of eddy current elements can advantageously cooperate with automated electromechanical means such as a robotic arm or the like to enable automatic scanning along designated scan axes extending along the surface of the workpiece under inspection. An eddy current probe constituted by such spatially correlated array of eddy current elements thus enhances the fiber-depth data collection capability of the inspection system of the present invention.

As seen in FIG. 1, a display device 32, such as an oscilloscope, can be conveniently used to display visual indications (e.g., 34) representative of the received fiber-depth data. In particular the visual indications can be compared against previously derived calibration indications obtained from a calibration specimen fabricated with a fiber layer whose respective fiber-depth is known.

Figure 3:
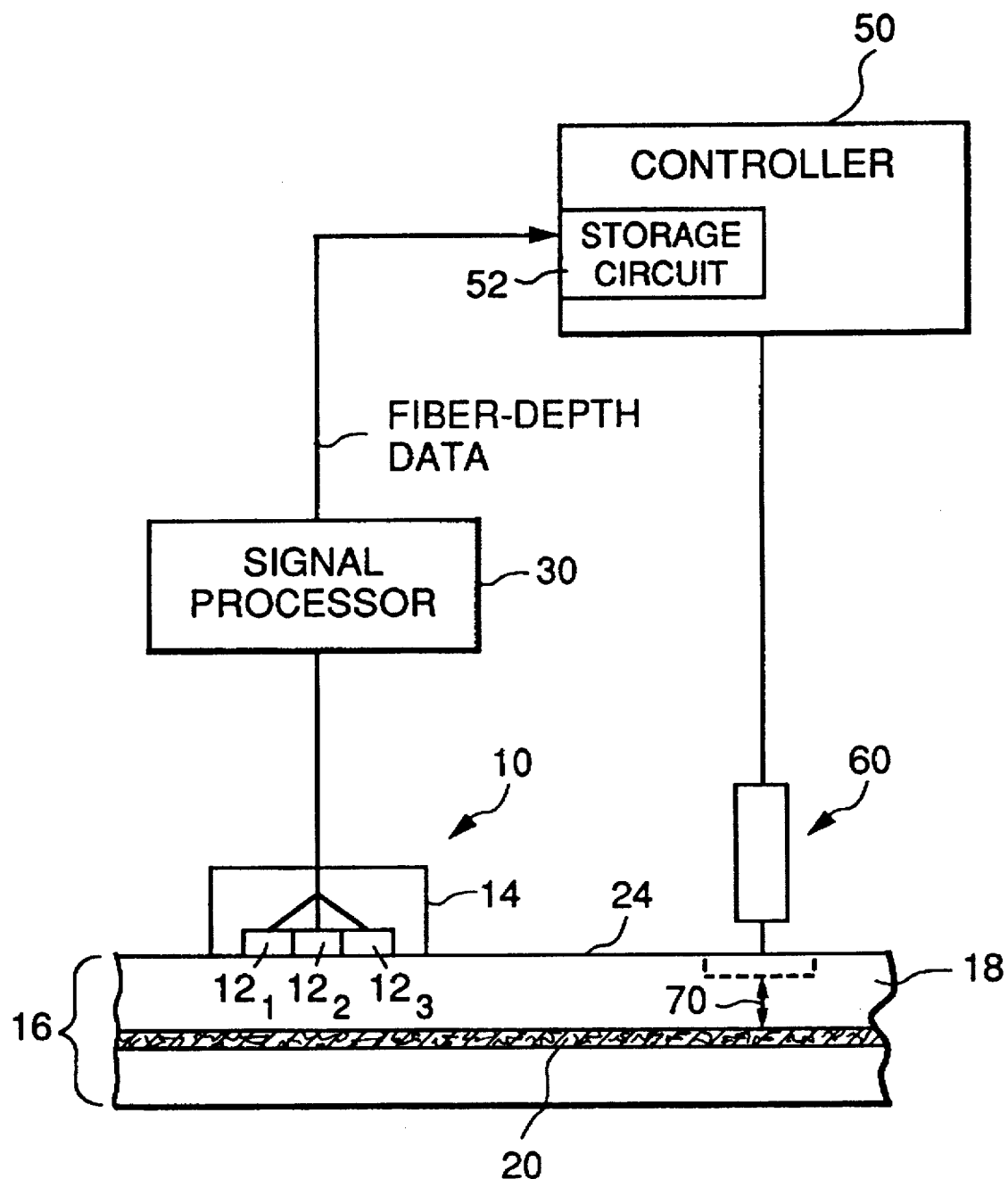
FIG. 3 is a schematic representation of another embodiment according to the present invention.

FIG. 3 illustrates another embodiment wherein the inspection system further includes a controller 50 operatively connected to the signal processor to receive fiber-depth data therefrom. The controller includes a conventional storage circuit 52 for storing the received fiber-depth data which can then be used to control a machining device 60, such as grinding machine or other like cutting machine, capable of selectively removing metal material (represented by the hidden line rectangle) to provide a selected spacing 70 between the machined workpiece surface and the predetermined section of reinforcing fibers whose fiber-depth data has been measured and stored in the storage circuit 52 of the controller 50. The controller 50 typically includes a signal conditioning circuit (not shown) designed to provide suitable data compatibility with appropriate electrical circuitry (not shown) in the machining device 60.

Figure 4:
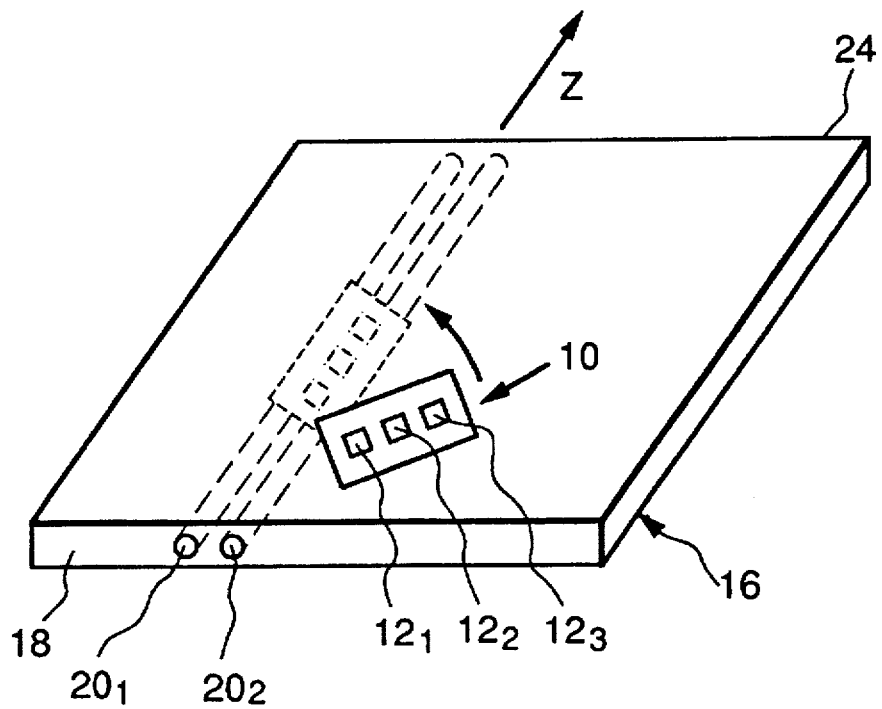
FIG. 4 shows a perspective view of a workpiece being inspected in accordance with a feature of the present invention.

FIG. 4 illustrates an eddy current probe 10 comprising at least one substantially colinear row of eddy current elements $12_1$, $12_2$ and $12_3$ each operating to produce a respective electrical signal as previously explained. To optimize mechanical properties of the workpiece, such as tensile strength, reinforcing fibers of a respective fiber-layer are preferably oriented in a direction parallel to a predetermined fiber-axis (here the z axis). However, due to their relatively small diameter (e.g., less than 100 μm), the reinforcing fibers are difficult to handle and therefore their actual fiber-axis orientation may deviate from their predicted one (here aligned substantially parallel to the z axis). The eddy current probe 10 may be positioned, either by manual or automated means, in an inspection position (represented by the dashed line probe) substantially parallel to the predetermined fiber-axis. In the event exemplary reinforcing fibers $20_1$ and $20_2$ have in fact an actual fiber-axis orientation which is substantially parallel to the predetermined fiber-axis (here the z axis), then each respective electrical signal generated by the eddy current elements in the substantially colinear row would be substantially identical to each other. Alternatively, if the actual fiber-axis orientation of reinforcing fibers $20_1$ and $20_2$ is not substantially parallel to the predetermined fiber axis, then each of the eddy current elements in the substantially colinear row cooperate to generate respective electrical signals being different from one another. This result follows since the electrical conductivity directly beneath each eddy current element would have a certain variation depending on the respective actual fiber-axis orientation of reinforcing fibers $20_1$ and $20_2$. Therefore, this feature of the invention can be conveniently used to inspect and determine the actual fiber-axis orientation of predetermined reinforcing fibers in the workpiece.

Figure 5:
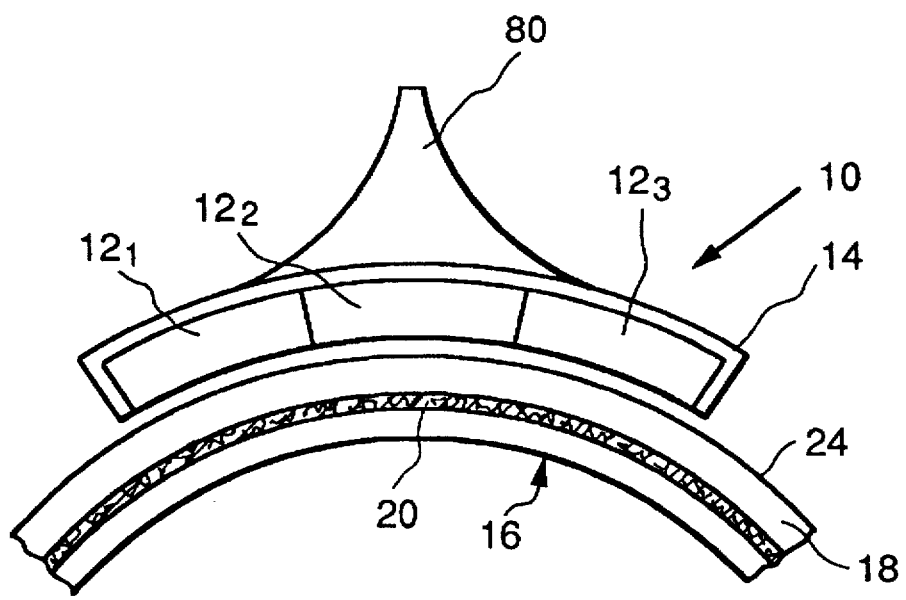
FIG. 5 shows a schematic elevation view of a workpiece having a substantially curved workpiece surface being inspected in accordance with another feature of the present invention.

FIG. 5 illustrates a feature of the invention which permits inspection of an MMC workpiece 16 having a substantially curved workpiece surface 24. In accordance with this feature of the invention, the eddy current probe 10 may be flexible and enclosed by a flexible housing 14 which can be mechanically connected to biasing means 80, such as a spring mechanism, a resilient member or the like. Thus, in operation, biasing means which may be conveniently manipulated by a robotic arm or the like can urge and conform the flexible eddy current probe against a workpiece having a substantially curved workpiece surface. This feature, therefore, conveniently allows fiber-depth measurements of MMC workpieces having complex geometrical shapes as is typically the case for MMC components used in myriad of industrial applications, aerospace applications being one of them. Those skilled in the art will additionally appreciate that the nondestructive inspection system of the present invention can also be utilized to inspect composite components made up of electrically nonconductive materials, such as polymers, reinforced with electrically conductive reinforcing fibers.

The flexible eddy current probe 10 may be of the kind but not limited to, for example, an eddy current probe fabricated using a photolithographic process such as, for example, a photolithographic process using a High Density Interconnect (HDI) technique, as disclosed in patent application Ser. No. 07/865,786 entitled "Flexible High Density Interconnect Structure and Flexibly Interconnected System" by C. W. Eichelberger et al., filed Apr. 7, 1992; and as disclosed in U.S. Pat. No. 4,783,695 entitled "Multichip Integrated Circuit Packaging Configuration and Method" by C. W. Eichelberger et al. Each of the above patent application and patent are assigned to the assignee of the present invention and hereby incorporated by reference.

The referred HDI technique allows the fabrication of an eddy current probe comprising fully integrated, flexible and miniaturized eddy current elements having a precisely matched electrical response not generally feasible with conventional eddy current elements, e.g., eddy current elements using mechanically wound coils. Description of such HDI fabricated eddy current probe is provided in patent application Ser. No. 07/696,455 entitled "Flexible Eddy Current Surface Measurement Array for Detecting Near Surface Flaws in a Conductive Part" by K. H. Hedengren et al., filed May 6, 1991, assigned to the assignee of the present invention and hereby incorporated by reference. Briefly, the referred HDI technique comprises metallizing, patterning and etching steps which advantageously allow the probe 10 to have a flexible multi-layer structure constructed with precision and uniformity. Each eddy current element as exemplified in FIG. 2, typically comprises a metallized pattern which can be situated in at least one layer of a flexible structure which contains a substrate; such as Kapton™, a polymide available from E. I. Dupont de Neumours Company. This metallized pattern is accomplished by first metallizing the flexible substrate, using sputtering or electroplating techniques to deposit thereon a coating of titanium and copper, for example. Then the patterning step, accomplished with a suitable photoresist, exposes by irradiation the metallized pattern which comprises each respective eddy current element. Thereafter, the etching step erodes away all metal but the patterned eddy current elements and associated interconnections. The above HDI technique, provided as an example of a photolithographic process and not by way of limitation, can provide an integral eddy current probe comprising eddy current elements having a level of precision heretofore unattainable by conventional means.

It will be understood that the features of the invention shown and described herein are exemplary only. Numerous variations, changes, substitutions and equivalents will now occur to those skilled in the art without departing from the spirit and scope of the present invention. Accordingly, it is intended that all subject matter described herein and shown in the accompanying drawings be regarded as illustrative only and not in a limiting sense and that the scope of the invention claimed be determined solely by the appended claims.

What is claimed is:

1. A system for measuring and selectively controlling fiber-depth in an electrically conductive workpiece having at least one layer of reinforcing fibers embedded therein, said system comprising:

an eddy current probe means for generating an electrical signal indicative of the spacing between a predetermined section of said reinforcing fibers within said workpiece and a surface of said workpiece, said eddy current probe means comprising a spatially correlated array of a plurality of discrete eddy current sensing elements each comprising at least one sense coil electrically interconnected in an absolute mode, said spatially correlated array of discrete eddy current sensing elements arranged in a substantially colinear row aligned to reach an inspection position substantially parallel to a predetermined fiber-axis, said substantially colinear row of eddy current elements cooperating in said inspection position to generate respective electrical signals indicative of the actual fiber-axis orientation of predetermined ones of said reinforcing fibers within said workpiece;

a signal processor connected to said eddy current probe means to receive and to process said spacing indicative electrical signal, said processor generating data indicative of fiber-depth of at least said predetermined section within said workpiece with respect to said workpiece surface in accordance with said processed electrical signal;

a controller connected to said signal processor to receive said fiber-depth data, said controller having a storage circuit for storing said received fiber-depth data; and machining means operatively coupled to said controller for selectively removing material from said workpiece surface according to said stored fiber-depth data to provide a selected spacing between a machined workpiece surface and at least said predetermined section of reinforcing fibers within said workpiece.

2. A system according to claim 1 wherein each of said sense coils generate a spacing indicative electrical signal in response to a selected operating frequency.

3. A system according to claim 1 whereto said array of eddy current elements is flexible.

4. A system according to claim 3 wherein each eddy current element of said flexible array is respectively constituted by a photolithographically metallized pattern.

5. A method for measuring and selectively controlling fiber-depth within an electrically conductive workpiece having at least one layer of reinforcing fibers embedded within said workpiece, said method comprising the steps of:

providing an eddy current probe comprising a spatially correlated array of a plurality of discrete eddy current sensing elements each comprising at least one sense coil electrically interconnected in an absolute mode and arranged in a substantially colinear row aligned to reach an inspection position substantially parallel to a predetermined fiber-axis, said eddy current probe adapted to be placed in contact with a surface of said workpiece;

positioning said substantially colinear row of eddy current elements over said workpiece surface so as to reach a predetermined inspection position substantially parallel to the predetermined fiber-axis;

operating said eddy current probe to cause each of said eddy current elements to generate electrical signals, said signals collectively indicative of the spacing between a predetermined section of said reinforcing fibers within said workpiece and said workpiece surface and the actual fiber-axis orientation of said reinforcing fibers within said workpiece;

processing said electrical signals to generate data indicative of fiber-depth of at least said predetermined section within said workpiece with respect to said workpiece surface;

storing said fiber-depth data; and selectively removing material from said workpiece surface by a machining means in accordance with said stored fiber-depth data so as to provide a selected spacing between at least said predetermined section of reinforcing fibers within said workpiece and a machined workpiece surface.

6. The method according to claim 5 wherein predetermined ones of said eddy current elements generate a respective spacing indicative electrical signal in response to a selected operating frequency.

7. The method according to claim 5 wherein the step of providing includes providing a flexible eddy current probe formed by photolithographically patterning said spatially correlated array of eddy current elements.

* * * * *